United States Patent [19]

Berger et al.

[11] 4,296,202

[45] Oct. 20, 1981

[54] DIAGNOSTIC COMPOSITION FOR THE DETECTION OF LEUKOCYTES AND CHROMOGENS USEFUL THEREIN

[75] Inventors: Dieter Berger, Viernheim; Franz Braun, Rimbach; Günter Frey, Ludwigshafen; Werner Güthlein, Mannheim-Neckarau; Manfred Kuhr, Mannheim, all of Fed. Rep. of Germany

[73] Assignee: Boehringer Mannheim GmbH, Fed. Rep. of Germany

[21] Appl. No.: 63,211

[22] Filed: Aug. 2, 1979

[30] Foreign Application Priority Data

Aug. 22, 1978 [DE] Fed. Rep. of Germany ....... 2836644

[51] Int. Cl.$^3$ .............................................. C12Q 1/29
[52] U.S. Cl. ..................................... 435/29; 260/152; 260/154; 260/155; 260/157
[58] Field of Search ........................................ 435/29, 4

[56] References Cited

U.S. PATENT DOCUMENTS

| | | | |
|---|---|---|---|
| 3,821,194 | 6/1974 | Peter et al. | 260/207 |
| 3,822,246 | 7/1974 | Weaver et al. | 260/152 |
| 3,840,517 | 10/1974 | Weaver et al. | 260/157 |
| 4,225,669 | 9/1980 | Melnick et al. | 435/29 |

*Primary Examiner*—Robert J. Warden

*Attorney, Agent, or Firm*—Sprung, Felfe, Horn, Lynch & Kramer

[57] ABSTRACT

Novel diagnostic composition for the detection of leukocytes in body fluids, comprising an absorbent carrier impregnated with a buffer substance and a chromgen, wherein the chromogen is an azo dyestuff ester of the formula

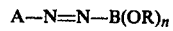

wherein
A is a five- or six-membered heterocyclic radical of up to 2 hetero ring atoms selected from nitrogen, sulfur and oxygen, and wherein the heterocyclic ring may be substituted with at least one member of the group selected from halogen, lower alkyl and lower alkoxy; or
A is phenyl substituted by at least one member of the group selected from lower alkyl, lower alkoxy, nitro, sulphanato and acylamino;
B is benzene, naphthalene or quinolone, optionally substituted with one or two radicals selected from sulphanato, lower alkoxy and lower alkoxypoly-alkyleneoxy;
R is a carboxylic acid residue or an amino acid or peptide residue having a nitrogen protective group; and
n is 1 or 2.

36 Claims, No Drawings

DIAGNOSTIC COMPOSITION FOR THE DETECTION OF LEUKOCYTES AND CHROMOGENS USEFUL THEREIN

The present invention is concerned with a composition for the detection of leukocytes in body fluids. In additional aspect, the invention is concerned with chromogens useful in such compositions and with the preparation of such chromogens.

The detection of leukocytes in body fluids and especially in urine, occupies an important place in the diagnosis of diseases of the kidneys and urogenital tract.

Heretofore, this detection was carried out by the laborious counting of the leukocytes in noncentrifuged urine or in urinary sediment. It is, of course, common to both methods that only intact leukocytes are counted. On the other hand, it is known that the rate of leukocyte lysis is subject to enormous variations, depending upon the urinary medium. Thus, for example in strongly alkaline urines, the leukocyte half life time can be as low as 60 minutes. The result is too low a leukocyte count or, when the urine sample has been left to stand for a comparatively long time, even a falsely negative finding.

Apart from lysis errors, the quantitative microscopic determination of leukocytes in non-centrifuged, homogenized urine in a counting chamber gives very dependable values. However, in practice, this method is rarely used since it is laborious, tiring and timeconsuming and requires the use of trained personnel.

The overwhelming majority of the leukocyte determinations in urine are, in medical practice, carried out by the viewing field method in the urine sediment. For this purpose, the material to be investigated (sediment) must first be obtained by centrifuging. However, other components of the urine are thereby also enriched, for example, salts and epithelial cells, which can make the microscopic counting of the leukocytes considerably more difficult. Varying content of sediment, inhomogeneities of the sediment, as well as, in some cases, differing microscopic enlargement or differing optical equipment of the microscope have the result that the here usual statement of the number of leukocytes per miroscopic viewing field can include errors of several hundred percent.

Therefore, it is an object of the present invention to provide a diagnostic agent with which the leukocytes in body fluids can be detected in a simple and readily usable manner, as well as as quickly and completely as possible.

One possible detection principle for such a leukocyte test could be an enzymatic reaction since leukocytes possess a very broad enzyme spectrum.

U.S. Pat. No. 3,087,794 describes a leukocyte detection method which is carried out via the peroxidate activity present in the granular leukocytes (granulocytes). An absorbent carrier, which is impregnated with hydrogen peroxide and an organic indicator, for example o-tolidine, indicates the presence of leukocytes by the formation of a colored oxidation product. However, such a test suffers from important disadvantages. On the one hand, peroxidate reactions possess, quite generally, a marked tendency to be disturbed by reducing substances present in the urine, for example ascorbic acid. On the other hand, there are many references to be found in the literature (see, for example, L. Mettler, Med. Welt, 23, 399/1972) to the instability of leukocyte peroxidase in the urine medium which gives rise to falsely negative findings.

For some years, in histo- and cytochemical enzymology, colorimetric methods of detection which depend upon the esterolytic activity of the enzymes present in the systems to be determined, have found a secure place (cf., for example, A.G.E. Pearse, Histochemistry, Theoretical and Applied). In principle, colorless or weakly colored esters are thereby employed which, due to enzymatic splitting, mostly break down into a colorless acid and an also colorless alcohol or phenol component. The latter is then reacted, in a reaction following the enzymatic saponification, to give colored products, for example by coupling with diazonium salts or by oxidative reactions. Thus, for example, F. Schmalzl and H. Braunsteiner have described (Klin. Wschr., 46, 642/1968) a specific cytochemical leukocyte esterase detection with naphthol-AS-D-chloroacetate as substrate and a diazonium salt for the formation of the colored azo compound.

However, for a diagnostic agent for the rapid and simple detection of leukocytes in body fluids, for example in the urine, two component systems of this kind do not provide to be suitable since, as is known, many compounds occurring in the urine, such as urobilinogen, stercobilinogen, bilirubin and the like, react with diazonium salts. Furthermore, this detection method is much too insensitive. Thus, for example, samples containing 5000 leukocytes/μl. show no reaction.

Surprisingly, we have now found that stable and rapidly indicating diagnostic agents, with which leukocytes can readily be detected in body fluids are obtained when azo dyestuff esters are employed as substrates for the detection of the esterases present in the neutrophilic leukocyte granulocytes.

Thus, according to the present invention, there is provided a diagnostic agent for the detection of leukocytes in body fluids, comprising an absorbent carrier which is impregnated with a chromogen and an appropriate buffer substance, wherein the chromogen used is an azo dyestuff ester of the general formula:

in which A is a five- or six-membered, optionally benzoannelated radical, containing one or two hetero atoms selected from nitrogen, sulphur and oxygen, which radical A is optionally substituted one or more times by halogen, lower alkyl and/or lower alkoxy, or A is a phenyl radical substituted one to three times by lower alkyl, lower alkoxy, nitro, sulphonato and/or acylamino, B is a benzene, naphthalene or quinoline radical optionally substituted once or twice by sulphonato, lower alkoxy and/or lower alkoxypolyalkyleneoxy, R is a carboxylic acid residue or an amino acid or peptide residue provided with a nitrogen protective group conventional in peptide chemistry and n is 1 or 2.

All azo dyestuff esters of general formula (I) are new compounds. Therefore, the present invention also provides the azo dyestuff esters of general formula (I), as well as processes for the preparation thereof.

The new azo dyestuff esters of general formula (I) can be prepared by methods known for the synthesis of phenyl esters. Preferably, an appropriate azo dyestuff of the general formula:

in which A, B and n have the same meanings as above, is reacted with an acid of the general formula:

HO—R    (III), in which R has the same meaning as above, or with an appropriate reactive derivative thereof.

When reactive derivatives of acids (III) are used for the preparation of the carboxylic acid esters, such reactive derivatives are preferably the corresponding carboxylic acid anhydrides or carboxylic acid chlorides, optionally used with the addition of tertiary amines. For the preparation of the amino acid and peptide esters, use is made of the methods of synthesis conventional in peptide chemistry.

The azo dyestuffs of general formula (II) are either known compounds (cf., for example, H. R. Hovind, The Analyst, 100, 769/1975) or can be prepared analogously to the known compounds.

Halogen in the definition of A is to be understood to be fluorine, chlorine or bromine and preferably bromine.

Lower alkyl in the definition of A, as well as lower alkoxy group in the definitions of A and B, contains 1 to 5 and preferably 1 to 3 carbon atoms, methyl, methoxy and ethoxy being especially preferred.

The polyalkyleneoxy radical of the lower alkoxypolyalkyleneoxy group in the definition of B can contain 1 to 5 and preferably 1 to 3 optionally alkylsubstituted alkyleneoxy groups, ethyleneoxy groups being preferred. As lower alkoxypolyalkyleneoxy radical, the 3,6-dioxaheptyloxy radical is especially preferred.

The sulphonato group in the definitions of A and B is to be understood to be not only the sulphonic acid residue itself but also the metal salts thereof and preferably the alkaline earth and alkali metal salts, the sodium salt being especially preferred.

The acylamino group in the definition of A is an amide grouping of an aromatic carboxylic acid, for example of benzoic or naphthoic acid, the benzoylamino radical being especially preferred.

The carboxylic acid residue of the substituent R can be the residue of an aliphatic carboxylic acid containing up to 5 and preferably up to 3 carbon atoms or also of an aromatic carboxylic acid, for example, of benzoic or naphthoic acid, the acetyl and benzoyl radicals being especially preferred.

As amino acid residues of the substituent R, the residues of naturally-occurring L-α-amino acids are preferred and especially those of glycine, L-alanine and L-phenylalanine.

A peptide residue in the definition of the substituent R is to be understood to be one of a di-, tri-, tetra- or pentapeptide and preferably of a di- or tri-peptide.

As amino acid components, the above-mentioned amino acids are preferably used.

The attachment of the OR side chains to the benzene, naphthalene or quinoline rings can be in any desired position. However, the azo groups are always to be in the ortho- and/or para-position to the OR substituents.

The azo dyestuff esters of general formula (I) used according to the present invention as chromogens are employed in concentrations of $10^{-4}$ to $10^{-1}$ mol/liter and preferably of $10^{-3}$ to $10^{-2}$ mol/liter of impregnation solution.

A further component of the diagnostic agent according to the present invention for the detection of leukocytes is an appropriate buffer system. For this purpose, there can be used, for example, a phosphate, barbiturate, borate, tris-(hydroxymethyl)-aminomethane (tris), 2-amino-2-methylpropane-1,3-diol (amediol) or amino acid buffer, the pH value and capacity being so chosen that, after dipping the test strip into a body fluid, there is obtained a pH value of 6–10 and preferably of 7–9.

Furthermore, it is advantageous, in the production of the diagnostic agents according to the present invention for the detection of leukocytes in body fluids, additionally to employ a tenside, since shorter reaction times can hereby be achieved. It is preferable to use a cationactive wetting agent, for example a quaternary ammonium, pyridinium or imidazolium salt, in a concentration of from 0.05 to 2% and preferably of from 0.1 to 0.5%.

A further component of the diagnostic agent for the detection of leukocytes according to the present invention can be an appropriate complex former. For this purpose, it is preferable to use a metal salt, for example, an iron, copper, chromium, cobalt, nickel, manganese or zinc salt, which reacts with the o-hydroxyazo dyestuffs resulting by the action of the leukocyte esterases on azo dyestuff esters of general formula (I), with deepening of color, to give corresponding metal chelate complexes, shorter reaction times and lower limits of detection hereby being achieved. The complex formers can be used in concentrations of from $10^{-4}$ to $10^{-1}$ mol/liter and preferably of $10^{-3}$ to $10^{-2}$ mol/liter of impregnation solution.

For the production of the diagnostic agent according to the present invention, a carrier and preferably an absorbent carrier, for example, filter paper, cellulose or synthetic fibre fleece, is impregnated with solutions of the necessary reagents usually employed for the production of test strips (substrate, buffer, optionally tensides, complex formers and the like), in a readily volatile solvent, for example water, methanol, ethanol or acetone. Impregnation is preferably carried out in two separate steps: first, the carrier is impregnated with an aqueous solution which contains the buffer and other water-soluble adjuvant materials. Thereafter, it is impregnated with a solution of the esterase substrate of the general formula (I). In special cases, the reverse impregnation sequence can also be employed. The test papers thus obtained can be used as such or, in known manner, can be applied to handles or preferably sealed in between synthetic resin films and fine-mesh materials in the manner described in German Patent Specification No. 2,118,455.

Diagnostic agents are thus obtained which, after dipping into a body fluid to be investigated, indicate rapidly and in a simple manner the presence of leukocytes by means of a color change. Since the activity of the esterases occurring in the neutrophilic leukocyte granulocytes is fully maintained even after lysis of the leukocytes, the diagnostic agent according to the present invention detects not only intact but also lysed leukocytes. Consequently, a lysis error does not occur.

The following Examples are given for the purpose of illustrating the present invention:

EXAMPLE 1

Filter paper, for example Schleicher & Schull 23 SL, is successively impregnated with the following solutions and then dried at 60° C.

Solution 1

| | |
|---|---|
| tris-(hydroxymethyl)-aminomethane | 0.61 g. |
| water, distilled | about 30 ml. |
| adjust the solution with 0.1N hydrochloric acid to a pH value of 7.0, | |
| water, distilled ad | 100 ml. | adjust the solution with 0.1 N hydrochloric acid to a pH value of 7.0, water, distilled ad

| | |
|---|---|
| Solution 2 | |
| thiazole-2-azo-1'[2'-(N-benzyloxy-carbonyl-L-alanyloxy)-naphthalene] | 46.1 mg. |
| acetone, ad | 100.0 ml. |

A pale pink colored test paper is obtained which, upon dipping into leukocyte-containing urines, becomes clearly red colored. There can be detected:
10,000 leukocytes/μl. urine in about 1 minute
5,000 leukocytes/μl. urine in about 2 minutes
2,000 leukocytes/μl. urine in about 5 minutes.
The sensitivity of the test is about 2000 leukocytes/μl.

Test papers with similar properties (sensitivities: 2,000–10,000 leukocytes/μl.) are obtained when, instead of thiazole-2-azo-1'-[2'-(N-benzyloxycarbonyl-L-alanyloxy)-naphthalene], the following substrates are employed, the stated color change of the test papers being observed upon dipping the test papers into leukocyte-containing urines:

1.1 thiazole-2-azo-2'-(1'-acetoxy-4'-methoxybenzene)
   color change: pale pink to violet.
1.2 thiazole-2-azo-2'-[1'-(N-benzyloxycarbonyl-L-alanyloxy)-4'-methoxybenzene]
   color change: pale pink to violet.
1.3 thiazole-2-azo-1'-(2',4'-diacetoxybenzene)
   color change: pale pink to red-violet.
1.4 thiazole-2-azo-4'-[1',3'-di-(N-benzyloxycarbonyl-L-alanyloxy)-benzene]
   color change: pale pink to red-violet.
1.5 thiazole-2-azo-1'-(2'-acetoxynaphthalene)
   color change: pale pink to red.
1.6 thiazole-2-azo-1'-[2'-(N-tert.-butyloxycarbonyl-L-alanyloxy)-naphthalene]
   color change: pale pink to red.
1.7 thiazole-2-azo-2'-[1'-acetoxynaphthalene]
   color change: pale pink to red-violet.
1.8 thiazole-2-azo-2'-[1'-(N-benzyloxycarbonyl-L-alanyloxy)-naphthalene]
   color change: pink to red-violet.
1.9 thiazole-2-azo-1'-[2'-(N-benzyloxycarbonyl-L-alanyloxy)-7'-sodium sulphonatonaphthalene] dihydrate
   color change: pink to red.
1.10 5-bromothiazole-2-azo-1'-[2'-(N-benzyloxycarbonyl-L-alanyloxy)-naphthalene]
   color change: pale pink to red.
1.11 benzothiazole-2-azo-1'-[2'-(N-benzyloxycarbonyl-L-alanyloxy)-naphthalene]
   color change: pink to red.
1.12 benzothiazole-2-azo-2'-[1'-(N-benzyloxycarbonyl-L-alanyloxy)-naphthalene]
   color change: pale pink to red.
1.13 6-methoxybenzothiazole-2-azo-2'-[1'-(N-benzyloxycarbonyl-L-alanyloxy)-naphthalene]
   color change: pink to red.
1.14 pyridine-2-azo-4'-[1'-3'-di-(N-benzyloxycarbonyl-L-alanyloxy)-benzene]
   color change: beige to red-violet.
1.15 pyridine-2-azo-1'-(2'-acetoxynaphthalene)
   color change: beige to red.
1.16 pyridine-2-azo-1'-(2'-benzyloxynaphthalene)
   color change: pink to red.
1.17 pyridine-2-azo-1'-[2'-(N-benzyloxycarbonyl-L-alanyloxy)-naphthalene]
   color change: beige to red.
1.18 2,4-dinitrobenzeneazo-2'-[1'-(N-benzyloxy-3',6'-disodium sulphonate)-naphthalene]
   color change: beige to blue.
1.19 thiazole-2-azo-1'-[2'-(N-benzyloxycarbonyl-glycyloxy)-naphthalene]
   color change: pale pink to red.
1.20 thiazole-2-azo-1'-[2'-(N-benzyloxycarbonyl-L-phenylalanyloxy)-naphthalene]
   color change: pale pink to red.

EXAMPLE 2

Filter paper, for example Schleicher & Schüll 23 SL, is successively impregnated with the following solutions and then dried at 60° C.

| | |
|---|---|
| Solution 1. | |
| tris-(hydroxymethyl)-aminomethane | 0.61 g. |
| water, distilled | about 30 ml. |
| adjust the solution with 0.1N hydrochloric acid to a pH value of 7.0, | |
| water, distilled | 100.0 ml. |
| Solution 2 | |
| thiazole-2-azo-4'-[1'-(N-benzoloxy-carbonyl-L-alanyloxy)-naphthalene] | 46.1 mg. |
| acetone, ad | 100.0 ml. |

A pink colored test paper is obtained which, upon dipping into leukocyte-containing urines, becomes clearly violet colored. There can be detected:
5,000 leukocytes/μl. urine in about 1 minute
2,000 leukocytes/μl. urine in about 3 minutes
1,000 leukocytes/μl. urine in about 6 minutes
500 leukocytes/μl. urine in about 10 minutes.
The sensitivity of the test is about 500 leukocytes/μl.

Test papers are obtained with similar properties (sensitivities: 500–5,000 leukocytes/μl.) when, instead of thiazolo-2-azo-4'-[1'-(N-benzyloxycarbonyl-L-alanyloxy)-naphthalene], the following substrates are employed, the stated color changes of the test papers being observed upon dipping into leukocyte-containing urines.

2.1 thiazole-2-azo-4'-(1'-acetoxynaphthalene)
   color change: pale pink to violet.
2.2 thiazole-2-azo-5'-[8'-(N-benzyloxycarbonyl-L-alanyloxy)-quinoline
   color change: pink to red.
2.3 thiazole-2-azo-4'-[1'-(N-benzyloxycarbonyl-L-alanyloxy)-5'-methoxynaphthalene]
   color change: pink to red.
2.4 thiazole-2-azo-4'-[1'-(N-benzyloxycarbonyl-L-alanyloxy)-5'-(3'',6''-di-oxaheptyloxy)-naphthalene]
   color change: pink to red.
2.5 5-bromothiazole-2-azo-4'-[1'-(N-benzyloxycarbonyl-L-alanyloxy)-naphthalene]
   color change: pale pink to violet.
2.6 benzothiazole-2-azo-4'-[1'-(N-benzyloxycarbonyl-L-alanyloxy)-naphthalene]

color change: pink to violet.
2.7 6-methoxybenzothiazole-2-azo-4'-[1'-(N-benzyloxycarbonyl-L-alanyloxy)-naphthalene]
color change: pink to violet.
2.8 thiazole-2-azo-4'-[1'-(N-benzyloxycarbonyl-L-alanyl-L-alanyloxy)-naphthalene]
color change: pale pink to violet.
2.9 thiazole-2-azo-4'-[1'-(N-benzyloxycarbonyl-L-alanyl-L-alanyl-L-alanyloxy)-naphthalene]
color change: pink to violet.
2.10 5-methylthiazole-2-azo-4'-[1'-(N-benzyloxycarbonyl-L-alanyloxy)-naphthalene]
color change: pink to violet.
2.11 6-methylbenzothiazole-2-azo-4'-[1'-(N-benzyloxycarbonyl-L-alanyloxy)-naphthalene]
color change: pink to violet.

EXAMPLE 3

Filter paper, for example Schleicher & Schüll 23 SL, is successively impregnated with the following solutions and then dried at 60° C.

| Solution 1 | |
|---|---|
| disodium tetraborate decahydrate | 1.91 g. |
| water, distilled | about 30 ml. |
| adjust the solution with 0.1N hydrochloric acid to a pH value of 8.0, | |
| water, distilled, ad | 100.0 ml. |
| Solution 2 | |
| 2-methoxy-4-nitrobenzeneazo-4'-[1'-(N-benzyloxycarbonyl-L-alanyloxy)-naphthalene] | 52.9 mg. |
| acetone, ad | 100.0 ml. |

A bright orange-colored test paper is obtained which, upon dipping into leukocyte-containing urines, becomes clearly red colored. There can be detected:
5,000 leukocytes/μl. urine in about 1 minute
2,000 leukocytes/μl. urine in about 3 minutes
1,000 leukocytes/μl. urine in about 5 minutes.
The sensitivity of the test is about 1000 leukocytes/μl.

Test papers are obtained with similar properties (sensitivities: 1000–5,000 leukocytes/μl.) when, instead of 2-methoxy-4-nitrobenzeneazo-4'-[1'-benzyloxycarbonyl-L-alanyloxy)-naphthalene], the following substrates are used, the stated color changes of the test papers being observed upon dipping into leukocyte-containing urines.

3.1 4-sodium sulphonatobenzeneazo-4'-[1-(N-benzyloxycarbonyl-L-alanyloxy)-naphthalene]
color change: yellow to red.
3.2 4-nitrobenzeneazo-4'-(1'-acetoxynaphthalene)
color change: yellow to red.
3.3 4-nitrobenzeneazo-4'-[1'-(N-benzyloxycarbonyl-L-alanyloxy)-naphthalene]
color change: yellow to red.
3.4 2,4-dinitrobenzeneazo-4'-(1'-acetoxybenzene)
color change: yellow to red-violet.
3.5 2,4-dinitrobenzeneazo-4'-[1'-(N-benzyloxycarbonyl-L-alanyloxy)-benzene]
color change: yellow to red-violet.
3.6 2,4-dinitrobenzeneazo-4'-(1'-acetoxynaphthalene)
color change: yellow to violet.
3.7 2,4-dinitrobenzeneazo-4'-[1'-(N-benzyloxycarbonyl-L-alanyloxy)-naphthalene]
color change: yellow to violet.
3.8 2-methoxy-4-nitrobenzeneazo-4'-(1'-acetoxybenzene)
color change: bright orange to red.
3.9 2-methoxy-4-nitrobenzeneazo-4'-(1'-acetoxynaphthalene)
color change: bright orange to red.
3.10 2-methoxy-4-nitrobenzeneazo-4'-[8'-(N-benzyloxycarbonyl-L-alanyloxy)-quinoline]
color change: bright orange to red-violet.
3.11 2-methoxy-4-nitrobenzeneazo-4'-[1'-(N-benzyloxycarbonyl-L-alanyloxy)-5'-methoxynaphthalene]
color change: bright orange to red.
3.12 2-methoxy-4-nitrobenzeneazo-4'-[1'-(N-benzyloxycarbonyl-L-alanyloxy)-5'-(3'',6''-dioxaheptyloxy)-naphthalene]
color change: bright orange to red.
3.13 4-methoxy-2-nitrobenzeneazo-4'-[1'-(N-benzyloxycarbonyl-L-alanyloxy)-naphthalene]
color change: bright orange to violet.
3.14 2,5-dimethoxy-4-nitrobenzeneazo-4'-[1'-(N-benzyloxycarbonyl-L-alanyloxy)-naphthalene]
color change: bright orange to violet.
3.15 2,5-dimethoxybenzeneazo-4'-[1'-(N-benzyloxycarbonyl-L-alanyloxy)-naphthalene]
color change: bright orange to red.
3.16 2-methoxy-4-benzoylamino-5-methyl-benzeneazo-4'-[1'-(N-benzyloxycarbonyl-L-alanyloxy)-naphthalene]
color change: pink to red.
3.17 2,5-dimethoxy-4-benzoylaminobenzeneazo-4'-[1'-(N-benzyloxycarbonyl-L-alanyloxy)-naphthalene]
color change: orange to red.
3.18 2,5-diethoxy-4-benzoylaminobenzeneazo-4'-[1'-(N-benzyloxycarbonyl-L-alanyloxy)-naphthalene]
color change: pink to red.
3.19 2-methoxy-4-nitrobenzeneazo-4'-[1'-(N-benzyloxycarbonylglycyloxy)-naphthalene]
color change: bright orange to red.
3.20 2-methoxy-4-nitrobenzeneazo-4'-[1'-(N-benzyloxycarbonyl-L-phenylalanyloxy)-naphthalene]
color change: bright orange to red.
3.21 2-methoxy-4-nitrobenzeneazo-4'-[1'-(N-p-toluenesulphonyl-L-alanyloxy)-naphthalene]
color change: orange to red.
3.22 2-methoxy-4-nitrobenzeneazo-4'-[1'-(N-p-toluenesulphonyl-L-alanyloxy)-5'-(3'',6''-dioxaheptyloxy)naphthalene]
color change: bright orange to red.

EXAMPLE 4

Filter paper, for example Schleicher & Schüll 23 SL, is successively impregnated with the following solutions and then dried at 60° C.

| Solution 1 | |
|---|---|
| tris-(hydroxymethyl)-aminomethane | 0.61 g. |
| water, distilled | about 30 ml. |
| lauryl pyridinium chloride | 0.2 g. |
| the solution is adjusted with 0.1N hydrochloric acid to a pH value of 7.0, | |
| water, distilled ad | 100 ml. |
| Solution 2 | |
| thiazole-2-azo-4'-[1'-(N-benzyloxycarbonyl-L-alanyloxy)-naphthalene] | 46.1 mg. |
| acetone, ad | 100 ml. |

A pink colored test paper is obtained which, upon dipping into leukocyte-containing urines, becomes clearly violet colored. In comparison with the formulation of Example 2, the reaction time is shortened by one half.

With the other substrates of Examples 1, 2 and 3, together with wetting agents, for example, the above-used lauryl pyridinium chloride, or also, for example, with benzyl trimethyl ammonium chloride or N-palmityl-N-methyl-benzimidazolium chloride, test papers are obtained which, in comparison with analogous test papers without a wetting agent, give reaction times which are shortened by about one half.

EXAMPLE 5

Filter paper, for example Schleicher & Schüll 23 SL, is successively impregnated with the following solutions and dried at 60° C.

| Solution 1 | |
| --- | --- |
| tris-(hydroxymethyl)-aminomethane | 0.61 g. |
| water, distilled | about 30 ml. |
| the solution is adjusted with 0.1N hydrochloric acid to a pH value of 7.0, water, distilled, ad | 100 ml. |
| Solution 2 | |
| thiazole-2-azo-1'-[2'-(N-benzyloxy-carbonyl-L-alanyloxy)-naphthalene] | 46.1 mg. |
| zinc acetate dihydrate | 21.9 mg. |
| acetone, ad | 100 ml. |

A pale pink colored test paper is obtained which, upon dipping into leukocyte-containing urines, becomes clearly blue-violet colored. In comparison with the formulation of Example 1, the reaction time is shortened by one half. Furthermore, the sensitivity of the test is improved to about 1000 leukocytes/μl.

With the other substrates of Example 1, together with a metal salt, for example, the above-used zinc acetate or also, for example, with cupric chloride or ferric chloride, test papers are obtained which, in comparison with analogous test papers without metal salts, display considerably shortened reaction times and the limits of detection are improved approximately by a factor of 2 to 3.

EXAMPLE 6

Thiazole-2-azo-4'-(1'-acetoxynaphthalene)

2.55 g. (0.01 mol) 4-(2'-Thiazolylazo)-1-naphthol are heated to 80° C. for 1 hour with 100 ml. acetic anhydride, to which 1 ml. pyridine has been added. Thereafter, excess acetic anhydride and the acetic acid formed are substantially distilled off in a vacuum and 50 ml. methanol are added to the distillation residue, followed by complete evaporation to dryness. The residue is recrystallized from 15 ml. toluene to give 2.0 g. (67% of theory) thiazole-2-azo-4'-(1'-acetoxynaphthalene) in the form of bright brown crystals; m.p. 137° C.

By the reaction of appropriately substituted azo dyestuffs with acetic anhydride, the following compounds are obtained in an analogous manner:

6.1 thiazole-2-azo-2'-(1'-acetoxy-4'-methoxybenzene)
  orange colored crystals; m.p. 111°-113° C.
6.2 thiazole-2-azo-1'-(2',4'-diacetoxybenzene)
  ochre colored crystals; m.p. 101° C.
6.3 thiazole-2-azo-1'-(2'-acetoxynaphthalene)
  dark, amorphous powder; TLC: finished plate of silica gel (elution agent: n-butanol-glacial acetic acid-water 2:1:1 v/v/v; detection: UV, inherent color; $R_T$ value: 0.50).
6.4 thiazole-2-azo-2'-(1'-acetoxynaphthalene)
  brown crystals; m.p. 122° C.
6.5 pyridine-2-azo-1'-(2'-acetoxynaphthalene)
  dark, amorphous powder; TLC: finished plate of silica gel, (elution agent: n-butanol-glacial acetic acid-water 2:1:1 v/v/v; detection: UV, inherent color; $R_F$ value: 0.72).
6.6 4-nitrobenzeneazo-4'-(1'-acetoxynaphthalene)
  brownish crystals; m.p. 160°-162° C.
6.7 2,4-dinitrobenzeneazo-4'-(1'-acetoxybenzene)
  red-brown crystals; m.p. 132° C.
6.8 2,4-dinitrobenzeneazo-4'-(1'-acetoxynaphthalene)
  ochre-colored crystals; m.p. 175° C.
6.9 2-methoxy-4-nitrobenzeneazo-4'-(1'-acetoxybenzene)
  orange colored crystals; m.p. 135° C.
6.10 2-methoxy-4-nitrobenzeneazo-4'-(1'-acetoxynaphthalene)
  orange colored crystals; m.p. 174°-178° C.

EXAMPLE 7

Pyridine-2-azo-1'-(2'-benzoyloxynaphthalene)

2.50 g. (0.01 mol) 1-(2'-Pyridylazo)-2-naphthol are dissolved in 50 ml. anhydrous pyridine, mixed with 5.5 ml. (0.05 mol) benzoyl chloride and stirred for a hour at 70° C. with the exclusion of water. Thereafter, the reaction mixture is cooled to ambient temperature and 3 ml. methanol are added thereto, followed by distillation to dryness in a vacuum. The residue is recrystallized from 100 ml. methanol to give 2.54 g. (72% of theory) pyridine-2-azo-1'-(2'-benzoyloxynaphthalene) in the form of red crystals; m.p. 153° C.

In an analogous manner, by the reaction of 2,4-dinitrobenzeneazo-2'-[1'-hydroxy-3',6'-di-(sodium sulphonate)-naphthalene] with benzoyl chloride, there is obtained:

7.1 2,4-dinitrobenzeneazo-2'-[1'-benzoyloxy-3',6'-di-(sodium sulphonato)-naphthalene]
  bright brown crystals; m.p.<250° C.; TLC: finished plate (elution agent: isopropanol, acetic acid butyl ester-water (5:3:2 v/v/v, detection: UV, inherent color; $R_F$ value: 0.43).

EXAMPLE 8

Thiazole-2-azo-1'-[2'-(N-benzyloxycarbonyl-L-alanyloxy)-naphthalene]

Solution 1

For the preparation of the acid chloride by the one-stage method, 5.70 g. (0.03 mol) N-benzyloxycarbonyl-L-alanine are dissolved in 50 ml. anhydrous dimethylformamide (DMF) and cooled to −30° C. Then, with stirring and cooling, 2.4 ml. (0.033 mol) thionyl chloride are pipetted thereto and the reaction mixture left in a cold bath at −30° C., with the exclusion of water.

Solution 2

3.83 g. (0.015 mol) 1-(2'-Thiazolylazo)-2-naphthol (TAN) are dissolved in 75 ml. anhydrous DMF and cooled to −30° C.

Reaction

Solution 2 is poured into Solution 1, 4.8 ml. (0.034 mol) triethylamine are added thereto as hydrogen chloride acceptor and the reaction mixture is stirred for 6 hours, without cooling, the temperature thereby being allowed to increase in 1.5 hours to 20° C. The reaction solution is then again cooled to −30° C. and the same amount of freshly prepared acid chloride Solution 1, as well as 4.8 ml. triethylamine, are added thereto. The temperature is again allowed to increase to 20° C. in 1.5 hours, whereafter the reaction is allowed to proceed to completion at ambient temperature in 18 hours. The reaction is preferably monitored chromatographically and the addition of the necessary excess of acid chloride and of triethylamine carried out correspondingly.

For the working up, the reaction mixture is evaporated to dryness in a vacuum at a maximum bath temperature of 50° C. The residue is taken up in 100 ml. ethyl acetate and successively washed twice with 30 ml. 1 N aqueous citric acid solution, 20 ml. water, 50 ml. 5 to 10% aqueous sodium bicarbonate solution and twice with 25 ml. water. After drying with anhydrous sodium sulphate, the ethyl acetate phase is evaporated in a vacuum. The residue is purified by column chromatography using silica gel and a toluene-dioxan mixture (9:1 v/v). After distilling off the solvent mixture in a vacuum and stirring the residue with ethyl acetate, there are obtained 4.9 g. (70.5%) thiazole-2-azo-1'-[2'-(N-benzyloxycarbonyl-L-alanyloxy)-naphthalene] in the form of yellow crystals; m.p. 162° C.

In analogous manner, from the appropriately substituted azo dyestuffs and N-protected amino acids or peptides, there are obtained the following compounds:

8.1 thiazole-2-azo-2'-[1'-(N-benzyloxycarbonyl-L-alanyloxy)-4'-methoxybenzene]
orange colored crystals; m.p. 14°–150° C.

8.2 thiazole-2-azo-4'-[1',3'-di-(N-benzyloxycarbonyl-L-alanyloxy)-benzane]
yellow-orange colored crystals; m.p. 133°–135° C.

8.3 thiazole-2-azo-2'-[1'-(N-benzyloxycarbonyl-L-alanyloxy)-naphthalene]
orange colored crystals; m.p. 174°–175° C.

8.4 thiazole-2-azo-4'-[1'-(N-benzyloxycarbonyl-L-alanyloxy)-naphthalene]
orange colored crystals; m.p. 132° C.

8.5 thiazole-2-azo-5'-[8'-(N-benzyloxycarbonyl-L-alanyloxy)-quinoline]
yellow crystals; m.p. 134° C.

8.6 thiazole-2-azo-1'-[2'-(N-benzyloxycarbonyl-L-alanyloxy)-7'-sodium sulphonato-naphthalene] dihydrate
orange colored powder; TLC; finished plata silica gel, (elution agent: isopropanol-butyl acetate-water 5:3:2 v/v/v, detection: UV, inherent color; $R_T$ value: 0.49).

8.7 thiazole-2-azo-4'-[1'-(N-benzyloxycarbonyl-L-alanyloxy)-5'-methoxynaphthalene]
orange colored crystals; m.p. 127° C.

8.8 thiazole-2-azo-4'-[1'-(N-benzyloxycarbonyl-L-alanyloxy)-5'-(3'',6''-dioxahepthyloxy)-naphthalene]
red-brown amorphous substance; TLD: finished plate silica gel (elution agent: chloroform-methanol 50:1 v/v, detection; UV, inherent color; $R_F$ value: 0.41).

8.9 5-bromothiazole-2-azo-1'-[2'-(N-benzyloxycarbonyl-L-alanyloxy)-naphthalene]
orange colored crystals; m.p. 192° C.

8.10 5-bromothiazole-2-azo-4'-[1'-(N-benzyloxycarbonyl-L-alanyloxy)-naphthalene]
orange colored crystals; m.p. 162° C.

8.11 benzothiazole-2-azo-1'-[2'-(N-benzyloxycarbonyl-L-alanyloxy)-naphthalene]
orange colored crystals; m.p. 190° C.

8.12 benzothiazole-2-azo-2'-[1'-(N-benzyloxycarbonyl-L-alanyloxy)-naphthalene]
orange colored crystals; m.p. 148°–150° C.

8.13 benzothiazole-2-azo-4'-[1'-(N-benzyloxycarbonyl-L-alanyloxy)-naphthalene]
orange colored crystals; m.p. 180°–182° C.

8.14 6-methoxy-benzothiazole-2-azo-2'-[1'-(N-benzyloxycarbonyl-L-alanyloxy)-naphthalene]
orange colored crystals; m.p. 148°–150° C.

8.15 6-methoxy-benzothiazole-2-azo-4'-[1'-(N-benzyloxycarbonyl-L-alanyloxy)-naphthalene]
yellow-orange colored crystals; m.p. 194°–196° C.

8.16 pyridine-2azo-4'-[1',3'-di-(N-benzyloxycarbonyl-L-alanyloxy)-benzene]
brownish, amorphous powder; TLC: finished plate silica gel, (elution agent: toluene-dioxan 5:1 v/v in atmosphere of glacial acetic acid, detection: UV, copper acetate-ammonia; $R_F$ value: 0.34).

8.17 pyridine-2-azo-1'-[2'-(N-benzyloxycarbonyl-L-alanyloxy)-naphthalene]
brownish crystals; m.p. 117° C.

8.18 4-sodium sulphonatobenzeneazo-4'-[1'-(N-benzyloxycarbonyl-L-alanyloxy)-naphthalene]
orange colored crystals; m.p. 264° C.

8.19 4-nitrobenzeneazo-4'-[1'-(N-benzyloxycarbonyl-L-alanyloxy)-naphthalene]
red-brown crystals; m.p. 145° C.

8.20 2,4-dinitrobenzeneazo-4'-[1'-(N-benzyloxycarbonyl-L-alanyloxy)-benzene]
ochre colored crystals; m.p. 110° C.

8.21 2,4-dinitrobenzeneazo-4'-[1'-(N-benzyloxycarbonyl-L-alanyloxy)-naphthalene]
orange colored crystals; m.p. 154° C.

8.22 2-methoxy-4-nitrobenzeneazo-4'-[1'-(N-benzyloxycarbonyl-L-alanyloxy)-naphthalene]
red-brown crystals; m.p. 186°–187° C.

8.23 2-methoxy-4-nitrobenzeneazo-5'-[8'-(N-benzyloxycarbonyl-L-alanyloxy)-quinoline]
orange colored crystals; m.p. 225°–230° C.

8.24 2-methoxy-4-nitrobenzeneazo-4'-[1'-(N-benzyloxycarbonyl-L-alanyloxy)-5'-methoxynaphthalene]
orange colored crystals; m.p. 165°–167° C.

8.25 2-methoxy-4-nitrobenzeneazo-4'-[1'-(N-benzyloxycarbonyl-L-alanyloxy-5'-(3'', 6''-dioxaheptyloxy)-naphthalene]
orange colored crystals; m.p. 118°–120° C.

8.26 4-methoxy-2-nitrobenzeneazo-4'-[1'-(N-benzyloxycarbonyl-L-alanyloxy)-naphthalene]
red-brown crystals; m.p. 140° C.

8.27 2,5-dimethoxy-4-nitrobenzeneazo-4'-[1'-(N-benzyloxycarbonyl-L-alanyloxy)-naphthalene]
orange colored crystals; m.p. 198°–201° C.

8.28 2,5-dimethoxybenzeneazo-4'-[1'-(N-benzyloxycarbonyl-L-alanyloxy)-naphthalene]
orange colored crystals; m.p. 145° C.

8.29 2-methoxy-4-benzoylamino-5-methylbenzeneazo-4'-[1'-(N-benzyloxycarbonyl-L-alanyloxy)-naphthalene]
red-brown crystals; m.p. 128°–130° C.

8.30 2,5-dimethoxy-4-benzoylaminobenzeneazo-4'-[1'-(N-benzyloxycarbonyl-L-alanyloxy)-naphthalene]
orange colored crystals; m.p. 141°–143° C.

8.31 2,5-diethoxy-4-benzoylaminobenzeneazo-4'-[1'-(N-benzyloxycarbonyl-L-alanyloxy)-naphthalene]
red-brown crystals; m.p. 173°–174° C.

8.32 thiazole-2-azo-1'-[2'-(N-benzyloxycarbonyl-L-phenylalanyloxy)-naphthalene]
orange colored crystals; m.p. 169° C.

8.33 2-methoxy-4-nitrobenzeneazo-4'-[1'-(N-benzyloxycarbonyl-L-phenylalanyloxy)-naphthalene]
red-brown crystals; m.p. 205°-207° C.

8.34 thiazole-2-azo-4'-[1'-(N-benzyloxycarbonyl-L-alanyl-L-alanyloxy)-naphthalene]
orange colored crystals; m.p. 175° C.

8.35 thiazole-2-azo-4'-[1'-(N-benzyloxycarbonyl-L-alanyl-L-alanyl-L-alanyloxy)-naphthalene]
bright orange colored crystals; m.p. 201° C.

8.36 5-methylthiazole-2-azo-4'-[1'-(N-benzyloxycarbonyl-L-alanyloxy)-naphthalene]

8.37 6-methylbenzothiazole-2-azo-4'-[1'-(N-benzyloxycarbonyl-L-alanyloxy)-naphthalene]

8.38 2-methoxy-4-nitrobenzeneazo-4''-[1'-(N-p-toluenesulphonyl-L-alanyloxy)-naphthalene]
reddish, amorphous powder, TLC: finished plate silica gel (elution agent: toluene-dioxan 6:1 v/v, detection: UV, inherent color; $R_F$ value: 0.38).

8.39 2-methoxy-4-nitrobenzeneazo-4'-[1'-(N-p-toluenesulphonyl-L-alanyloxy)-5'-(3'',6''-dioxaheptyloxy)-naphthalene]
orange colored crystals; m.p. 61°-63° C.

EXAMPLE 9

Thiazole-2-azo-1'-[2'-(N-tert.-butyloxycarbonyl-L-alanyloxy)-naphthalene]

1.89 g. (0.01 mol) N-tert.-Butyloxycarbonyl-L-alanine and 2.55 g. (0.01 mol) 1-(2'-thiazolylazo)-2-naphthol (TAN) are dissolved in 50 ml. anhydrous pyridine at ambient temperature and mixed with a solution of 2.2 g. (0.0107 mol) dicyclohexylcarbodiimide (DCC) in 20 ml. pryidine. With the exclusion of water, the reaction mixture is stirred for about 24 hours at ambient temperature, whereafter 1.89 g. (0.01 mol) N-tert.-butyloxycarbonyl-L-alanine and 2.2 g. (0.0107 mol) DCC are again added to the reaction solution, followed by stirring for a further 24 hours at ambient temperature. The N,N'-dicyclohexylurea which already separates out after a short time is filtered off with suction, the solvent is distilled off in a vacuum and the residue is taken up in 100 ml. ethyl acetate. Further precipitating N,N'-dicyclohexylurea is filtered off with suction and the clear ethyl acetate solution successively washed twice with 30 ml. aqueous 1 N citric acid solution, 20 ml. water, 50 ml. 5 to 10% aqueous sodium bicarbonate solution and with 25 ml. water. After drying with anhydrous sodium sulphate, the ethyl acetate phase is evaporated in a vacuum. The sticky residue obtained is purified by column chromatography using a silica gel column and a toluene-dioxan mixture (9:1 v/v). There are obtained 2.65 g. (62% of theory) thiazole-2-azo-1'-(N-tert.-butyloxycarbonyl-L-alanyloxy)-naphthalene] in the form of orange colored crystals; m.p. 142°-144° C.

In analogous manner, from the appropriate amino acids and the appropriately substituted azo dyestuffs and DCC, there are obtained the following compounds:

9.1 thiazole-2-azo-1'-[2'-(N-benzyloxycarbonyl-glycyloxy)-naphthalene]
orange colored crystals; m.p. 166° C.

9.2 2-methoxy-4-nitrobenzeneazo-4'-[1'-(N-benzyloxycarbonyl-glycyloxy)-naphthalene]
yellow-orange colored crystals; m.p. 185°-189° C.

It will be understood that the specification and examples are illustrative, but not limitative of the present invention and that other embodiments within the spirit and scope of the invention will suggest themselves to those skilled in the art.

What is claimed is:

1. Diagnostic composition for the detection of leukocytes in body fluids, comprising an absorbent carrier impregnated with a buffer substance and a chromogen, wherein the chromogen is an azo dyestuff ester of the formula $$A-N=N-B(OR)_n$$

wherein:
A is a five- or six-membered heterocyclic radical of up to 2 hetero ring atoms selected from nitrogen, sulfur and oxygen, and wherein the heterocyclic ring may be substituted with at least one member of the group selected from halogen, lower alkyl and lower alkoxy; or A is phenyl substituted by at least one member of the group selected from lower alkyl, lower alkoxy, nitro, sulphanato and acylamino;

B is benzene, naphthalene or quinoline, optionally substituted with one or two radicals selected from sulphanato, lower alkoxy and lower alkoxypolyalkyleneoxy;

R is a carboxylic acid residue or an amino acid or peptide residue having a nitrogen protective group; and n is 1 or 2.

2. Diagnostic composition as claimed in claim 1 wherein A is a five- or six-membered heterocyclic ring which is benzo-annelated.

3. Diagnostic composition as claimed in claim 1 wherein A is a five-membered heterocyclic ring.

4. Diagnostic composition as claimed in claim 1 wherein A is a six-membered heterocyclic ring.

5. Diagnostic composition as claimed in claim 1 wherein A contains one nitrogen ring atom.

6. Diagnostic composition as claimed in claim 1 wherein A contains two nitrogen ring atoms.

7. Diagnostic composition as claimed in claim 1 wherein A contains one sulfur ring atom.

8. Diagnostic composition as claimed in claim 1 wherein A contains one oxygen ring atom.

9. Diagnostic composition as claimed in claim 1 wherein A contains one nitrogen and one sulfur ring atom.

10. Diagnostic composition as claimed in claim 1 wherein A contains one nitrogen and one oxygen ring atom.

11. Diagnostic composition as claimed in claim 1 wherein A is thiazolyl.

12. Diagnostic composition as claimed in claim 1 wherein A is benzothiazolyl.

13. Diagnostic composition as claimed in claim 1 wherein A is substituted phenyl.

14. Diagnostic composition as claimed in claim 1 wherein B is benzene.

15. Diagnostic composition as claimed in claim 1 wherein B is naphthalene.

16. Diagnostic composition as claimed in claim 1 wherein B is quinoline.

17. Diagnostic composition as claimed in claim 1 wherein R is a carboxylic acid radical.

18. Diagnostic composition as claimed in claim 1 wherein R is an amino acid residue.

19. Diagnostic composition as claimed in claim 1 wherein R is a peptide residue.

20. Diagnostic composition as claimed in claim 1 wherein n is 1.

21. Diagnostic composition as claimed in claim 1 wherein n is 2.

22. Diagnostic composition as claimed in claim 1 wherein said azo dyestuff ester is thiazole-2-azo-1'-[2'-(N-benzyloxycarbonyl-L-alanyloxy)-naphthalene].

23. Diagnostic composition as claimed in claim 1 wherein said azo dyestuff ester is thiazole-2-azo-4'-[1'-(N-benzyloxycarbonyl-L-alanyloxy)-naphthalene].

24. Diagnostic composition as claimed in claim 1 wherein said azo dyestuff ester is 2-methoxy-4-nitrobenzeneazo-4'-[1'-(N-benzyloxy-carbonyl-L-alanyloxy)-naphthalene].

25. Diagnostic composition as claimed in claim 1 wherein said azo dyestuff ester is 2,5-dimethoxy-4-nitrobenzeneazo-4'-[1'-(N-benzyloxy-carbonyl-L-alanyloxy)-naphthalene].

26. Diagnostic composition as claimed in claim 1 wherein said azo dyestuff ester is 2-methoxy-4-nitrobenzeneazo-4'-[1'-(N-p-toluene-sulphonyl-L-alanyloxy)-naphthalene].

27. Diagnostic composition as claimed in claim 1 wherein said buffer is a phosphate.

28. Diagnostic composition as claimed in claim 1 wherein said buffer is a barbiturate.

29. Diagnostic composition as claimed in claim 1 wherein said buffer is a borate.

30. Diagnostic composition as claimed in claim 1 wherein said buffer is tris-(hydroxymethyl)-aminomethane (tris).

31. Diagnostic composition as claimed in claim 1 wherein said buffer is 2-amino-2-methylpropane-1,3-diol.

32. Diagnostic composition as claimed in claim 1 wherein said buffer is an amino acid buffer.

33. Diagnostic composition as claimed in claim 1 additionally containing an adjuvant material.

34. Diagnostic composition as claimed in claim 1 additionally containing a wetting agent.

35. Diagnostic composition as claimed in claim 1 additionally containing a complex-former.

36. Method for the detection of leukocytes in body fluids which method comprises contacting a sample with the diagnostic composition as claimed in claim 1.

* * * * *